United States Patent [19]

O'Rourke et al.

[11] Patent Number: 5,298,428
[45] Date of Patent: Mar. 29, 1994

[54] SELF-REFERENCING SPECTROPHOTOMETRIC MEASUREMENTS

[75] Inventors: Patrick E. O'Rourke, Martinez, Ga.; David R. Van Hare, Aiken, S.C.

[73] Assignee: United States Department of Energy, Washington, D.C.

[21] Appl. No.: 957,133

[22] Filed: Oct. 7, 1992

Related U.S. Application Data

[63] Continuation of Ser. No. 478,326, Feb. 12, 1990, abandoned.

[51] Int. Cl.$^5$ .......................................... G01N 21/00
[52] U.S. Cl. ............................ 436/171; 356/326; 422/82.08; 422/82.09; 422/82.11; 436/178
[58] Field of Search ............... 422/82.09, 82.11, 91, 422/56, 86, 82.08; 436/171, 178; 356/326, 498; 364/496, 498

[56] References Cited

U.S. PATENT DOCUMENTS

| | | | |
|---|---|---|---|
| 3,354,315 | 11/1967 | Preston et al. | 422/82.08 |
| 3,700,335 | 10/1972 | Seelbinder | 356/201 |
| 3,820,901 | 6/1974 | Kreuzer | 356/326 |
| 4,236,894 | 12/1980 | Sommervold | 364/498 |
| 4,267,572 | 5/1981 | Witte | 364/498 |
| 4,305,723 | 12/1981 | Kolber et al. | 364/498 |
| 4,309,112 | 1/1982 | Ashley et al. | 422/82.09 |
| 4,752,447 | 6/1988 | Kimmel et al. | 422/56 |
| 4,863,694 | 9/1989 | Kimmel et al. | 422/86 |
| 5,014,216 | 5/1991 | Stafford et al. | 364/496 |
| 5,023,804 | 6/1991 | Hoult | 364/498 |

OTHER PUBLICATIONS

Stephen Brewer, "Solving Problems In Analytical Chemistry", 1980, pp. 268-285.
John W. Moore, Ralph G. Pearson, *Kinetics and Mechanism*, 1981, pp. 421-422.

*Primary Examiner*—James C. Housel
*Assistant Examiner*—Laura E. Collins
*Attorney, Agent, or Firm*—Brian R. Tumm; Harold M. Dixon; William R. Moser

[57] ABSTRACT

A method for measuring the concentration of a chemical substance by spectrophotometry comprising the steps of placing a sample of a photoreactive substance between the light source and a spectrophotometer, obtaining an absorption spectrum of the substance using a fixed amount of light from the light source, obtaining a second absorption spectrum after a short interval, comparing the two to determine the concentration of the chemical substance from the difference in the spectra. If the chemical substance is not photoreactive, a photoreactive mixture can be made with a photoreactive dye that has photoreactive properties unique to the mixture. Alternatively, an optically transparent substrate can absorb the substance or the dye/substance mixture.

14 Claims, 3 Drawing Sheets

SELF-REFERENCING SPECTROPHOTOMETRIC MEASUREMENTS

BACKGROUND OF THE INVENTION

1. Field of the Invention and Contract Statement

The present invention relates to determining the concentrations of chemical substances by spectrophotometry. The United States Government has rights in this invention pursuant to Contract No. DE-AC09-76SR00001 between the U.S. Department of Energy and E.I. DuPont de Nemours & Co.

This is a continuation of application Ser. No. 07/478,326 filed Feb. 12, 1990, now abandoned.

2. Discussion of Background

Chemical substances that are not optically transparent absorb light in exponential proportion to the concentration of the substance present. Furthermore, the light transmitted through such a substance has an absorption spectrum characteristic of both the substance, the light source and any other medium through which the light travels. That absorption spectrum can be prismatically revealed for analysis. By discounting the portion of the absorption spectrum attributable to the light source and other absorbers, the spectrum of the chemical substance can be isolated and its identity and concentration determined. The discounting, or "referencing", is done by determining the absorption spectrum of the light source and any spectrophotometric components in the absence of the chemical substance. Referencing is usually done close in time to the measurement of the absorbance of the chemical substance to minimize error. This much is known in the art of spectrophotometry.

At times referencing can be very difficult, impossible or undesirable. In groundwater contamination monitoring, for example, spectrophotometry can be done according to traditional techniques, by taking samples from the ground and subjecting them to analysis in the laboratory. However, in situ groundwater contamination spectrophotometric measurements, if they could be done accurately, would obviate the need for sampling and the time and effort sampling takes. In situ monitoring would allow continuous monitoring for sudden fluctuations in contaminant levels.

Because spectrophotometry is capable of very accurate measurements when properly referenced, it would be ideally suited for groundwater monitoring, where very small concentrations of chemical substances must be measured. However, without a means of self-referencing, in situ spectrophotometry can only be as good as the assumptions made about the reference conditions.

SUMMARY OF THE INVENTION

An object of the invention is a method for making spectrophotometric measurements.

Another object of the invention is a method for making spectrophotometric measurements without the need to reference the source of light for the measurements. A still further object of the invention is a method for making spectrophotometric measurements of both photoreactive and nonphotoreactive chemical substances.

To achieve the foregoing and other objects and in accordance with the purpose of the invention, as embodied and broadly described herein, the method of the present invention comprises positioning a spectrophotometer to receive light from a light source, preferably carried by a fiber optic cable, shining through a photoreactive chemical substance, or, if the chemical substance is not photoreactive, through a chemical substance mixed with an indicator dye, which results in a photoreactive chemical complex, and then making several spectrophotometric measurements. Then, from the multiple measurements, the spectra of the chemical substance can be determined by discounting the spectra of the light and any intervening spectrophotometric components.

In an alternate embodiment, an optically transparent substrate for absorbing the photoreactive substance is positioned in the path of the light, or, if the chemical substance is nonphotoreactive, the substrate can be first coated with the indicator dye and then positioned in the chemical substance between the light source and the spectrophotometer.

Several spectral measurements taken short time intervals apart will produce different absorption spectra; each one altered from the first by the effect of the light on the photoreactive chemical substance, or on the dye/nonphotoreactive chemical substance complex. The difference in the spectra correlates with the concentration of the substance. Using a known exposure time and a known delay time between measurements, the concentration of the chemical substance can be immediately derived from the difference between the spectra.

The method allows spectrophotometric measurements to be made as often as desired without sampling and in a variety of environments where referencing is not possible or not desirable.

Reference is now made in detail to the present preferred embodiment of the invention, an example of which is given in the accompanying drawings.

A BRIEF DESCRIPTION OF THE DRAWINGS

The accompanying drawings, which are incorporated in and form a part of the specification, illustrate the invention and, together with the description, serve to explain the principles of the invention. In the drawings.

DETAILED DESCRIPTION OF A PREFERRED EMBODIMENT

The present invention is a method for measuring the concentration of chemical substances by spectrophotometry whenever referencing of the pure light source is not possible or desirable or where measurements are desired on a frequency that, for all practical purposes, precludes sample gathering. The method uses the photoreactive property of certain chemical substances; that is, the property of the substance to decompose to a different, product substance as a result of light energy impinging on the substance and causing a chemical change.

When the absorption spectrum of a sample of an unknown concentration of a known chemical substance is obtained by shining a light of known intensity for a known interval of time through the chemical substance to a spectrophotometer and then, a short, fixed time interval later, its absorption spectrum measured again, the second spectrum will differ from the first as a result of a reduction in the concentration of the chemical substance and the increase in the concentration of a product substance. By knowing what quantity and type of change to expect from a given deposition of light, the original concentration of the chemical substance can be inferred.

If the intensity of the light is unknown, the concentration of the substance can still be measured by repeated exposure to the light source until no more changes occur in the absorption spectra. The total change in the absorption spectra is then a direct measure of the quantity of photoreactive substance originally present.

If the chemical substance is not photoreactive, mixing it with an indicator dye often results in a photoreactive complex of known photoreactive behavior that has photoreactive properties different from those of the dye by itself and thereby converts the nonphotoreactive chemical substance to a photoreactive one.

Figure 1:
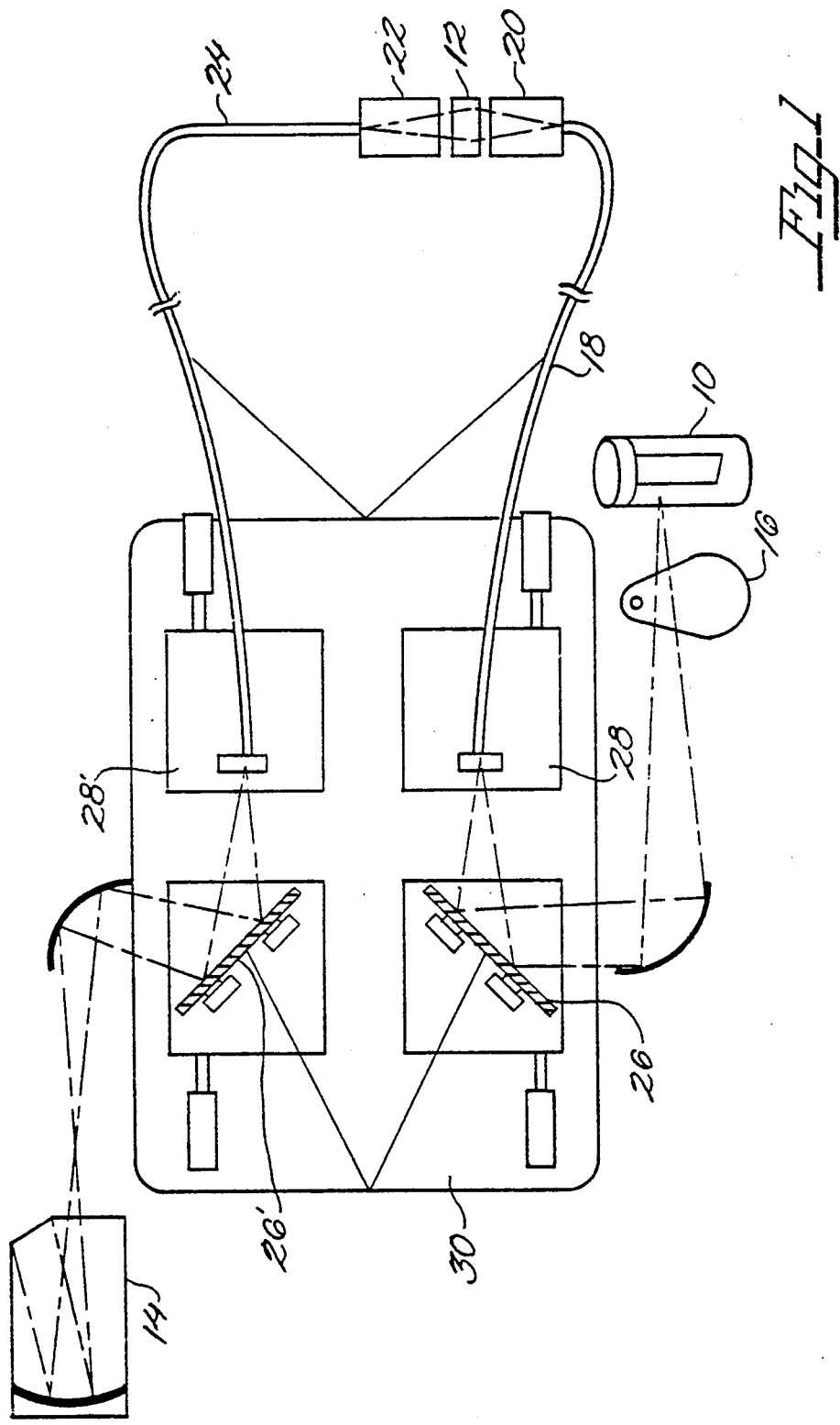
FIG. 1 is a schematic of a fiber optic coupler according to an embodiment of the present invention.

Referring now to the FIG. 1, showing an example of an apparatus enabling the present invention to be practiced, a light source 10 is positioned to shine through a sample of the chemical substance placed in sample cell 12 and be received by the spectrophotometer 14. The duration of the light from light source 10 is regulated by a shutter 16 and carried conveniently by a first optical fiber 18. A first collimating lens 20 trains the light on sample cell 12.

A second collimating lens 22 focuses the emerging light on a second optical fiber 24. Adjustable mirrors, 26 and 26', and adjustable stages, 28 and 28', help to direct the light from the light source 10 to first optical fiber 18 and to the spectrophotometer 14 from second optical fiber 24, respectively. For stability, the optical arrangement is preferably mounted on a base 30. Optical fibers 18 and 24 may be long enough for remote placement of sample cell 12.

If the chemical substance is not photoreactive, a dye may be mixed with the substance to produce a photoreactive complex that has photoreactive properties different than those of the dye alone. A sample of the complex would be placed in sample cell 12.

Alternatively, a photoreactive chemical substance may be absorbed onto and held by an optically transparent substrate (not shown) and the substrate placed in sample cell 12, or the substrate may be coated with a photoreactive dye, and the substrate positioned in sample cell 12. The chemical substance will be absorbed onto the coated substrate and mix with the dye. The substrate is preferably made of plastic of a type that readily absorbs chemical substances and dyes.

Figure 2:
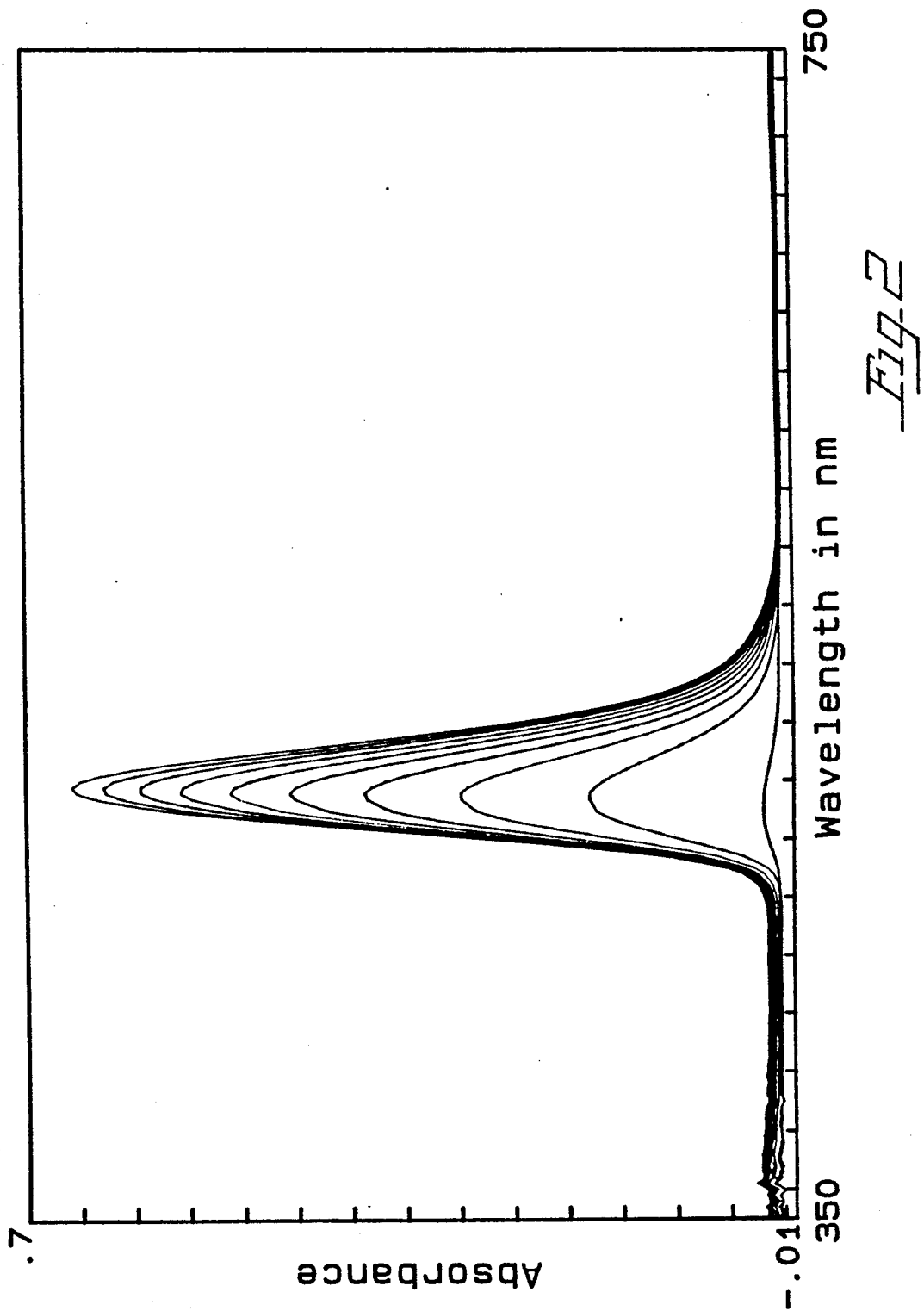
FIG. 2 is an example of a series of absorption spectra of "TREFLAN" adsorbed into a clear plastic disk, showing the change in the spectra with succeeding exposures to light.

FIG. 2 shows absorption spectra of a photoreactive chemical substance taken short time intervals apart. Absorbance (minus the log, base 10, of the ratio of the incident light divided by the reference light) is shown as a function of wavelength in nanometers ($10^{-9}$M). Because of the deposition of light made as part of each measurement, a portion of the chemical substance decomposes to a product substance. If the photoreactive behavior of the chemical substance is known, the concentration of the original substance can be calculated since the change is absorbance is directly related to the deposition of incident light energy on the sample.

The following examples illustrate the present invention.

EXAMPLE 1

The spectra of "TREFIAN", a plant root growth inhibitor and a photoreactive compound which adsorbs strongly onto plastics, coloring them yellow was measured. The "TREFLAN" was absorbed onto a piece of "TYGON" tubing. When the tubing was exposed to light, the "TREFLAN" began to decompose to other, colored compounds. The absorption spectra of the sample changed as a function of how much light impinged on the sample and how much "TREFLAN" was present in the sample. FIG. 2 shows plots of the changes observed in the absorption spectra of the colored plastic as it was exposed to light. The large peak which grew in at about 490 nM is a decomposition product of "TREFLAN". Note in the plots of FIG. 2 that the absorbance increase from spectrum to spectrum decreased as a function of time. If the light is directed at a sample in the sample cell long enough, the spectrum will cease to change and the resulting magnitude of the absorbance spectrum is a measure of the original "TREFLAN" concentration absorbed into the plastic. However, it is not necessary to completely photolyze the sample to estimate the "TREFLAN" concentration if the change from spectrum to spectrum can be mathematically modeled.

EXAMPLE 2

Figure 3:
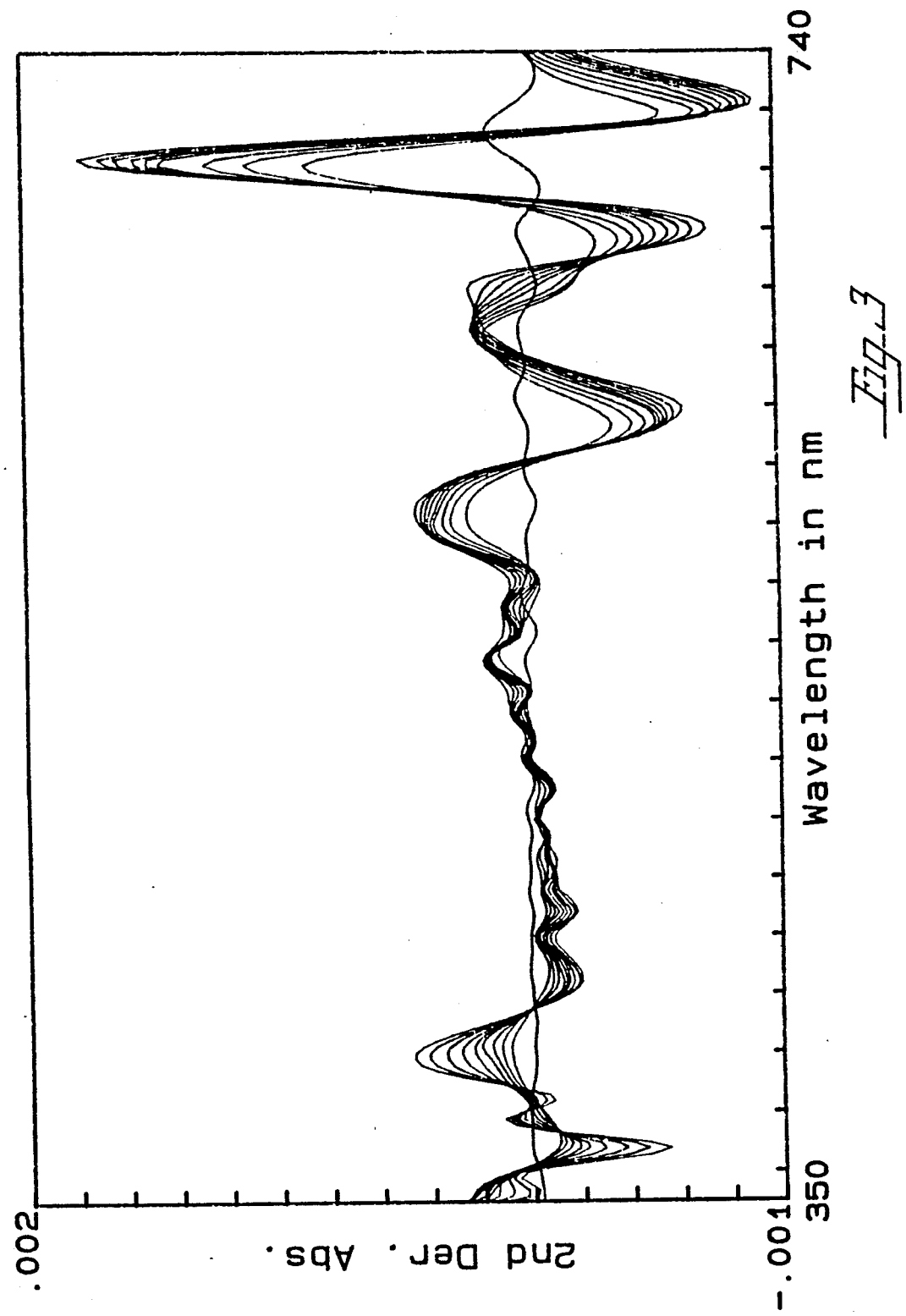
FIG. 3 is another example of a series of absorption spectra of uranyl nitrate-Arsenazo III-contaminated water showing the changes in the spectra with succeeding exposures to light.

FIG. 3 shows changes in the second derivative absorption spectra of 50 ppm uranium complexed with Arsenazo III indicator dye as a function of wavelength. While neither uranium nor Arsenazo III is particularly photoreactive, their complex is. The complex was soaked onto filter paper and the measurements taken every ten seconds. The second derivative absorption band at 700 nM is from the depletion of the uranyl-Arsenazo III. Again note as shown in FIG. 3 that the change in one spectrum from the preceding spectrum was less with each succeeding exposure.

The foregoing description of preferred embodiments of the invention has been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. A method for measuring the concentration of a photoreactive chemical substance, said method comprising the steps of:

transmitting light having an intensity through a photoreactive chemical substance, said light intensity effective to decompose said photoreactive chemical substance;

measuring a first absorption of said photoreactive chemical substance from transmitted light;

after an interval of time, measuring a second absorption spectrum of decomposed photoreactive chemical substance from transmitted light;

comparing said first and said second absorption spectra to determine an amount of said photoreactive chemical substance that has decomposed; and determining the original concentration of said photoreactive chemical substance form said amount, said interval and said intensity of light.

2. The method as recited in claim 1, wherein said transmitting step further comprises the step of transmitting said light from a source of light through an optic fiber to a cell containing said photoreactive chemical substance.

3. The method as recited in claim 1, wherein said transmitting step further comprises the steps of:

absorbing said photoreactive chemical substance onto a substrate; and transmitting said light through said substrate.

4. The method as recited in claim 1, wherein said transmitting step further comprises the steps of:

absorbing said photoreactive chemical substance onto a substrate; and transmitting said light from a source of light through an optic fiber and then through said substrate.

5. The method as recited in claim 1, wherein said measuring steps both further comprise the steps of:

passing said transmitted light through an optic fiber to a spectrophotometer; and measuring said first and second absorption spectra with said spectrophotometer.

6. The method as recited in claim 1, wherein said transmitting step further comprises the step of transmitting said light from a source of light through a first optic fiber, and said measuring step further comprises the steps of:

passing said transmitted light through a second optic fiber to a spectrophotometer; and measuring said first and second absorption spectra with said spectrophotometer.

7. The method as recited in claim 1, wherein said transmitting step further comprises the steps of:

absorbing said photoreactive chemical substance onto a substrate, transmitting said light from a source of light through a first optic fiber and then through said substrate; and wherein said measuring steps further comprise the steps of:

passing said transmitted light through a second optic fiber to a spectrophotometer, and measuring said first and second absorption spectra with said spectrophotometer.

8. A method for measuring the concentration of a chemical substance, said method comprising the steps of:

mixing a chemical substance with a photoreactive dye to form a photoreactive complex;

transmitting light having an intensity through said photoreactive complex, said light intensity effective to decompose said photoreactive complex;

measuring a first absorption spectrum of said photoreactive complex from transmitted light;

after an interval of time, measuring a second absorption spectrum decomposed photoreactive complex from transmitted light;

comparing said first and said second absorption spectra to determine an amount of said photoreactive complex that has decomposed; and determining the original concentration of said photoreactive complex from said amount, said interval and said intensity of light.

9. The method as recited in claim 8, wherein said transmitting step further comprises the step of transmitting said light from a source of light through an optic fiber to a cell containing said photoreactive complex.

10. The method as recited in claim 8, wherein said transmitting step further comprises the steps of:

absorbing said photoreactive complex onto a substrate; and transmitting said light through said substrate.

11. The method as recited in claim 8, wherein said transmitting step further comprises the steps of:

absorbing said photoreactive complex onto a substrate; and transmitting said light from a source of light through an optic fiber and then through said substrate.

12. The method as recited in claim 8, wherein said measuring steps further comprise the steps of:

passing said transmitted light through an optic fiber to a spectrophotometer; and measuring said first and second absorption spectra with said spectrophotometer.

13. The method as recited in claim 8, wherein said transmitting step further comprises the step of transmitting said light from a source of light through a first optic fiber, and said measuring steps both further comprise the steps of:

passing said transmitted light through a second optic fiber to a spectrophotometer; and measuring said first and second absorption spectra with said spectrophotometer.

14. The method as recited in claim 8, wherein said transmitting step further comprises the steps of:

absorbing said photoreactive complex onto a substrate, transmitting said light from a source of light through a first optic fiber and then through said substrate; and wherein said measuring steps further comprise the steps of:

passing said transmitted light through a second optic fiber to a spectrophotometer, and measuring said first and second absorption spectra with said spectrophotometer.

* * * * *